(12) United States Patent
Barth et al.

(10) Patent No.: US 7,090,640 B2
(45) Date of Patent: Aug. 15, 2006

(54) SYSTEM AND METHOD FOR AUTOMATIC DETERMINATION OF A REGION OF INTEREST WITHIN AN IMAGE

(75) Inventors: Jacques Dov Barth, Santa Monica, CA (US); Maud Maria Zonjee, Santa Monica, CA (US); John David Heaton King, Sherman Oaks, CA (US)

(73) Assignee: Q-Vision, Encino, CA (US)

( * ) Notice: Subject to any disclaimer, the term of this patent is extended or adjusted under 35 U.S.C. 154(b) by 206 days.

(21) Appl. No.: 10/712,834

(22) Filed: Nov. 12, 2003

(65) Prior Publication Data

US 2006/0056672 A1    Mar. 16, 2006

(51) Int. Cl.
*A61B 8/00* (2006.01)
(52) U.S. Cl. ..................... 600/443; 382/128
(58) Field of Classification Search ............ 600/437–8, 600/443–7, 463–7; 128/916; 382/128, 130, 382/173, 256, 266, 273
See application file for complete search history.

(56) References Cited

U.S. PATENT DOCUMENTS 6,301,498 B1 * 10/2001 Greenberg et al. .......... 600/425
6,503,202 B1 * 1/2003 Hossack et al. ............ 600/454
6,730,035 B1 * 5/2004 Stein .......................... 600/449
6,817,982 B1 * 11/2004 Fritz et al. .................. 600/443
6,835,177 B1 * 12/2004 Fritz et al. .................. 600/443
2004/0116813 A1 * 6/2004 Selzer et al. ................ 600/467
2004/0197015 A1 * 10/2004 Fan et al. .................... 382/128
2005/0038343 A1 * 2/2005 Cao et al. .................... 600/454
2005/0096528 A1 * 5/2005 Fritz et al. .................. 600/407
2005/0267365 A1 * 12/2005 Sokulin et al. ............. 600/437

* cited by examiner

Primary Examiner—Francis J. Jaworski
(74) Attorney, Agent, or Firm—Kenneth L. Green; Edgar W. Averill, Jr.

(57) ABSTRACT

A system and method for automated image analysis selects a Region Of Interest (ROI) within a frame, suitable for subsequent Quantitative Intima Media Thickness (QIMT) analysis. Presently, a time consuming manual analysis by a highly trained technician is required to select the ROI within the frame for subsequent automated analysis. The automated image analysis provides an immediate and accurate identification of the ROI within the selected frame. In one embodiment, the automated image quality analysis may be directed to an ultrasound image of the carotid artery.

21 Claims, 8 Drawing Sheets

SYSTEM AND METHOD FOR AUTOMATIC DETERMINATION OF A REGION OF INTEREST WITHIN AN IMAGE

TECHNICAL FIELD

The present invention relates to automated determination of a Region Of Interest (ROI) within an Image, and more particularly, to an automated determination of an ROI of an ultra sound image of a carotid artery.

BACKGROUND ART

According to the U.S. Center for Disease Control (CDC), heart disease is the leading cause of death in the United States, and atherosclerosis (a progressive narrowing and hardening of the arteries over time) is the leading factor in heart disease. Although initial thickening of arterial walls develops over a very long period of time, the complications from atherosclerosis generally occur suddenly and often prove fatal. Further, because atherosclerosis is asymptomatic, the first symptom perceived by a patient may be a life-threatening event.

Several methods are available for measuring the progress of atherosclerosis. These include Electron Beam Computed Tomography (EBCT), Magnetic Resonance Imaging (MRI), Flow Mediated Dilation (FMD), Quantitative Intima Media Thickness (QIMT), and the like. Although MRI may be use for clinical measurements, it remains a costly procedure. FMD appears promising, but outcome studies are not available to validate its predictive ability.

Carotid Intima Media Thickness (IMT) has been shown to be a useful surrogate endpoint. A surrogate endpoint is an indirect measurement which correlates with an actual (i.e., clinical) outcome. A clinical endpoint, for example, could be death, loss of vision, or other major symptomatic event. A corresponding surrogate endpoint could be a measurement which indicates the development of a condition which is correlated with a clinical endpoint event, but which surrogate endpoint may not produce easily observable symptoms. In particular, IMT measurements of the far wall of the carotid artery, about 1 cm below the bulb, have shown high correlation with cardiovascular clinical endpoints.

Carotid IMT provides a suitable surrogate endpoint for all stages of atherosclerosis and is well suited for tracking the progress of atherosclerosis. Carotid IMT has predictive value with respect to cerebrovascular and cardiovascular clinical events in both men and women. It has further been found that providing an ultrasound image of the carotid artery to a patient has a substantial effect of motivating changes to behavior, and the provision of subsequent images showing progress helps patients remain motivated to sustain a healthy life style.

Carotid IMT may be measured by either analog caliper IMT or digital Quantitative IMT (QIMT). Both methods rely on the same image and attempt to measure the same quantity. Caliper IMT is a manual measurement of the IMT visible in an ultrasound image using calipers, and is similar to printing a photo, and then measuring a dimension of a characteristic of the photograph by laying a ruler on the photograph. QIMT is a computer analysis of IMT performed on a digital version of the ultrasound image. Results have shown that caliper IMT has four times the standard deviation of QIMT when performed on the same images. Because of the accuracy of QIMT measurements, QIMT is ideal for both absolute measurements of the IMT, and for tracking small changes in the carotid artery, and thus the progression of atherosclerosis. The ability to track small changes allows the success or failure of a given course of treatment to be analyzed and adjusted if necessary, before a critical state is reached.

Current practice in the field of QIMT is to record carotid artery ultrasound images on SVHS tapes, and later manually review the images to determine a Region Of Interest (ROI) within each frame for subsequent computer analysis using edge detection algorithms. Such manual review requires highly skilled technicians and is time intensive. Because of the present requirement for manual review, IMT presently is only available from specialized laboratories employing highly trained technicians. There is thus a need for an objective system and method to automate the determination of the ROI of carotid ultrasound images, which method does not introduce operator bias.

DISCLOSURE OF THE INVENTION

The present invention addresses the above and other needs by providing a system and method for automated image analysis, which system and method selects a Region Of Interest (ROI) within the image (or frame) suitable for subsequent Quantitative Intima Media Thickness (QIMT) analysis. Presently, a time-consuming manual analysis by a highly trained technician is required to select the ROI within the frame for subsequent analysis. The automated image analysis of the present invention provides an efficient, timely, and accurate identification of the ROI within the frame.

In accordance with one aspect of the invention, there is provided a method for defining an ROI for subsequent processing, comprising specifying a physical characteristic of a morphological structure, providing at least one image of a portion of the morphological structure, said image containing the physical characteristic, and automatically processing the image to identify an ROI within the image, wherein the ROI contains the physical characteristic, and wherein the ROI is smaller than the original image, and the ROI is preferably from approximately 0.25 centimeters to approximately 1.0 centimeters wide by approximately 0.25 centimeters to approximately 1.0 centimeters high, and the ROI is more preferably approximately 0.5 centimeters wide by approximately 0.5 centimeters high.

The physical characteristic is preferably an Intima Media Thickness (IMT) of an artery, more preferably the IMT of a portion of a carotid artery, and most preferably the IMT of a far wall of the Bulb-Common Carotid Artery interface ranging between approximately 1.0 cm and approximately 1.5 cm below the base of the bulb, or most preferably the IMT of the far wall of a portion of the carotid artery ranging between approximately 1.75 cm and approximately 2.25 cm below the bifurcation. The image is preferably processed digitally, and the image may be provided as a digital image, or the image may be provided as an analog image, and processed to generate a digital image, and more preferably, the image is provided as a SVHS image and is processed to generate a digital image.

In one embodiment, the image is provided as a rectangular frame comprising a rectangular array of pixels, which frame is vertically sliced into a multiplicity of slices, which slices are preferably two pixels wide. The slices are processed to identify the presence of stripes. A stripe comprises three bands, a dark band with light bands both above and below the dark band, which light bands correspond to vessel walls, and which dark band corresponds to a vessel lumen. Each slice is processed by image processing software which identifies the stripes with confidence scores above a threshold, preferably a fifty percent confidence threshold.

Pairs of slices may be compared to detect the bifurcation of the carotid artery, wherein the pairs of slices preferably comprise adjacent slices. If for any reason, adjacent slices cannot be singly compared, substantially adjacent slices (e.g., less than 3 slices apart) may be compared, or a combination of substantially adjacent slices maybe compared (i.e., an averaging of features). If a first slice (i.e., a slice above, or after another slice) of a pair of slices has one more stripe than a second slice (i.e., a slice below or before another slice) and if top most and bottom most edges of two adjacent first stripes in the first slice (i.e., the slice with a greater number of stripes) correspond respectively to the top edge and bottom edge of a second stripe in the second slice, a bifurcation is identified. Preferably, the vertical positions of the corresponding edges will be within approximately five percent of each other. If the bifurcation is found, the ROI is horizontally centered approximately 2.0 centimeters before the bifurcation.

In some cases, the bifurcation may not be successfully identified. In these cases, the slices may be processed to attempt to identify the bulb of the carotid artery. The average number of stripes within the frame is computed. If a valid number of stripes is computed, an attempt is made to use the resulting value to determine the position of the bulb of the carotid artery. The portion of the carotid artery below the bulb is referred to as the Common Carotid Artery (CCA). If the number of stripes is three or more, the stripe that is next to the bottom is tagged as a selected vessel. If the number of stripes is two, the bottom stripe is tagged as the selected vessel. If the number of stripes is one, the one stripe is tagged as the selected vessel.

A moving average of the vessel diameter (i.e., lumen diameter) is computed, preferably from ten consecutive slices. The center of the moving average of slices is tagged as the bulb position if the lumen diameter increases sufficiently from one average to the next average, preferably at least ten percent lumen diameter increase. If the bulb is found, the ROI is horizontally centered approximately 1.25 centimeters before the bulb.

In some cases, neither the bifurcation nor the bulb are detectable. In these cases, the automatic processing may select a defined region approximately twenty percent higher and approximately twenty percent wider than the ROI from a previous frame. A pattern match may then be automatically performed within the defined region to determine a new ROI which matches a previous ROI. If all of the automatic processing fails to identify the ROI, the ROI may be a manually generated by a technician.

It is a further feature of the invention to provide a method for determining a Region Of Interest (ROI) for subsequent Intima Media Thickness (IMT) analysis, the method comprising providing at least one digital frame of a portion of a carotid artery, wherein the frame includes at least one of a set consisting of a bulb of the carotid artery and a bifurcation of the carotid artery, and automatically processing the frame to identify an ROI in the frame. The automatically processing comprises at least one of the set consisting of determining the ROI by detecting a bifurcation of the carotid artery, determining the ROI by detecting a bulb of the carotid artery, and determining the ROI by pattern-matching a portion of the frame to a previous ROI.

Determining the ROI by detecting a bifurcation of the carotid artery comprises slicing the frame into vertical slices, automatically comparing at least one of the vertical slices to at least one other of the vertical slices to find the bifurcation of the carotid artery, determining an ROI horizontal extent ranging from approximately 1.75 cm before the bifurcation to approximately 2.25 cm before the bifurcation, identifying a highest point of a far wall segment of the carotid artery within the ROI horizontal extent, and determining an ROI vertical extent ranging from approximately 0.3 cm above the highest point to approximately 0.2 cm below the highest point.

Determining the ROI by detecting a bulb of the carotid artery comprises slicing the frame into the vertical slices, automatically comparing at least one of the vertical slices to at least one other of the vertical slices to find the bulb of the carotid artery, determining the ROI horizontal extent to range from approximately 1.00 cm before the bulb to approximately 1.50 cm before the bulb, identifying the highest point of a far wall segment of the carotid artery within the ROI horizontal extent, and determining the ROI vertical extent to range from approximately 0.3 cm above the highest point to approximately 0.2 cm below the highest point.

Determining the ROI by pattern-matching a portion of the frame to a previous ROI having a previous horizontal extent and a previous vertical extent comprises determining an expanded ROI horizontal extent to the previous horizontal extent expanded horizontally by a factor of approximately 1.2, determining an expanded ROI vertical extent to the previous vertical extent expanded vertically by a factor of approximately 1.2, performing an automatic pattern match comparing the previous ROI to the region defined by the expanded ROI horizontal extent and the expanded ROI vertical extent, and determining the ROI based on the highest correlation of the automatic pattern match.

It is an additional feature of the invention to provide a system for processing ultrasound images of the carotid artery, comprising an ultrasound sensor, an ultrasound apparatus adapted to generate frames, a sensor cable connecting the ultrasound sensor to the ultrasound apparatus, a computer, and a path adapted to carry the ultrasound data from the ultrasound apparatus to the computer, wherein the path is selected from a group consisting of dedicated cables, phone lines, a Local Area Network (LAN), the Internet, and a wireless path.

The ultrasound apparatus is adapted to receive measurements from the ultrasound sensor and to process the measurements to generate ultrasound data. The computer is adapted to pre-process the ultrasound data to generate Regions Of Interest (ROI) within the data for subsequent processing, which ROIs are subsets of the ultrasound data.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

MODES FOR CARRYING OUT THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides a system and method for automated image quality analysis which selects a Region Of Interest (ROI) within the frame for subsequent analysis. In one embodiment, the subsequent analysis comprises computing a Quantitative Intima Media Thickness (QIMT) of a carotid artery. The QIMT is a useful parameter in determining the cardiovascular health of a patient, and particularly the presence of heart disease, and more particularly the presence of atherosclerosis. QIMT is capable of providing very accurate measurements, and as a result QIMT is ideal for both absolute measurements of the IMT, and for tracking small changes in the carotid artery, and thus the progression of atherosclerosis. The ability to track small changes allows the success or failure of a given course of treatment to be analyzed and adjusted if necessary, before a critical state is reached.

QIMT may be performed using, for example, the ARTIS computerized edge contour measurement technique developed by Prevention Concepts Inc., in West Los Angeles, Calif. Although the automated image quality analysis method of the present invention is described herein in the context of pre-processing images for QIMT of the carotid artery, those skilled in the art will recognize that other methods of processing images will similarly benefit from the present invention, and in particular, other methods of processing ultrasound images will similarly benefit from the present invention, and even more particularly, other methods of processing ultrasound images of any artery or of the carotid artery in particular will similarly benefit from the present invention, and the application of the present invention to pre-processing any image is intended to come within the scope of the present invention.

Figure 1:
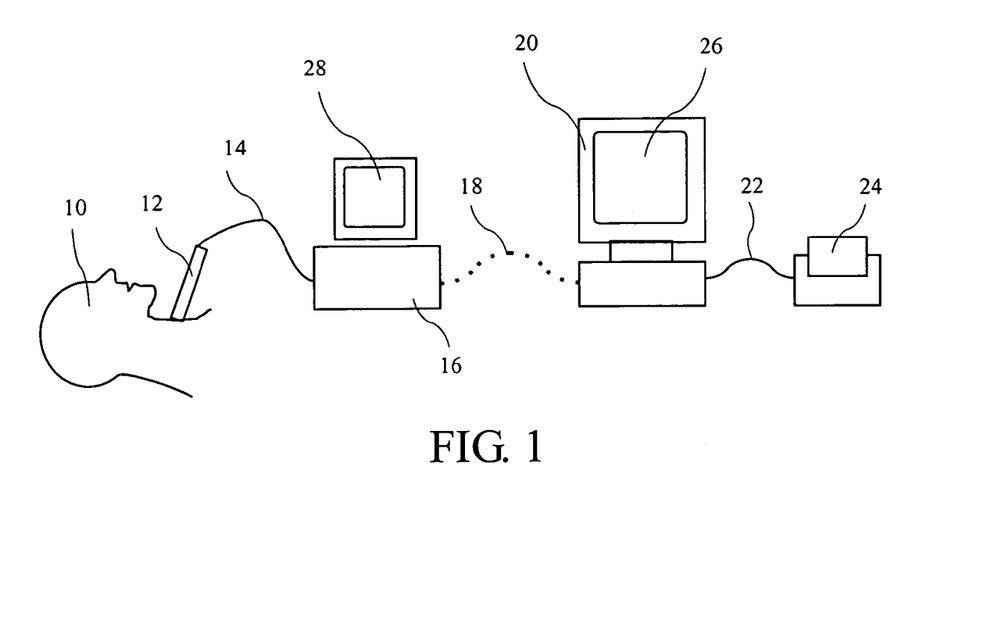
FIG. 1 shows a system suitable for acquiring and processing ultrasound image data according to the present invention.

Elements of a typical system according to the present invention is shown in FIG. 1. The elements include an ultrasound sensor 12 shown residing proximal to the neck of a patient 10. The ultrasound sensor 12 is connected by a sensor cable 14 to an ultrasound apparatus 16. The ultrasound apparatus 16 may provide power to the ultrasound sensor 12 and receive measurements from the ultrasound sensor 12. The ultrasound apparatus 16 communicates with a computer 20 over a path 18. The path 18 may be any of a variety of paths including dedicated cables, phone lines, a Local Area Network (LAN), the Internet, a wireless path, etc., and a system according to the present invention using any path is intended to come within the scope of the present invention.

The computer 20 processes the signal received from the ultrasound apparatus 16 and may provide results on a screen 26, or over an output cable 22 to an output device 24. When the computer 20 is remote from the ultrasound apparatus 16, the results may be transmitted back to the ultrasound apparatus over the path 18, or over a different path, and be displayed on a second screen 28

Figure 2:
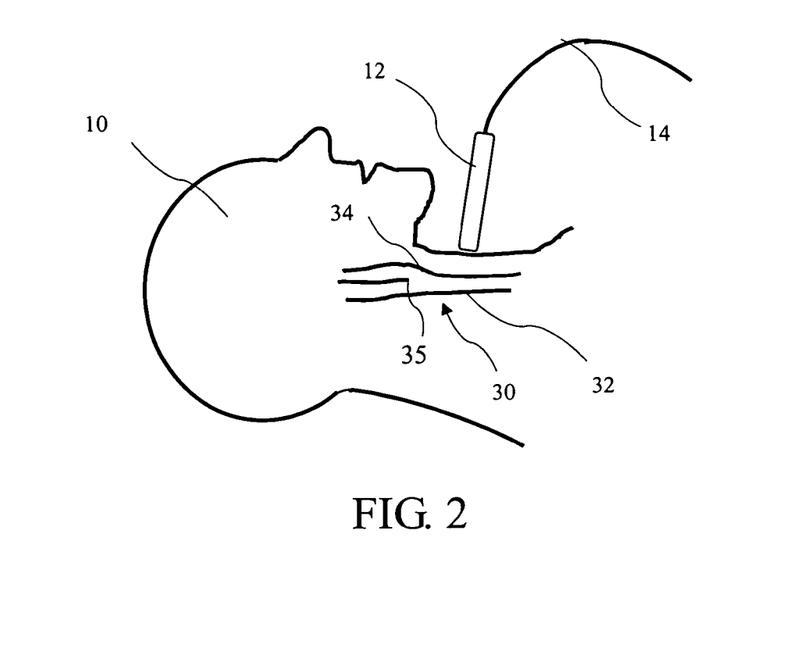
FIG. 2 depicts positioning of an ultrasound sensor relative to a carotid artery.

A more detailed view of the patient 10 and ultrasound sensor 12 is shown in FIG. 2. The ultrasound sensor 12 is positioned to image a far wall 32 of the carotid artery 30, about one cm before a bulb 34, or about two centimeters before a bifurcation 35. The blood flow within the carotid artery 30 is from the right to the left in FIG. 2, and a point within the carotid artery 30 to the right of the bulb 34 or to the right of the bifurcation 35 is hereafter referred to as being before or below the bulb 34 or the bifurcation 35. Various studies have shown that measurements the IMT of the far wall 32 correlate well with clinical end points. The far wall 32 IMT measurements have proven to be reproducible, and show a remarkable correlation with cardiovascular events as far as ten years in the future.

Figure 3:
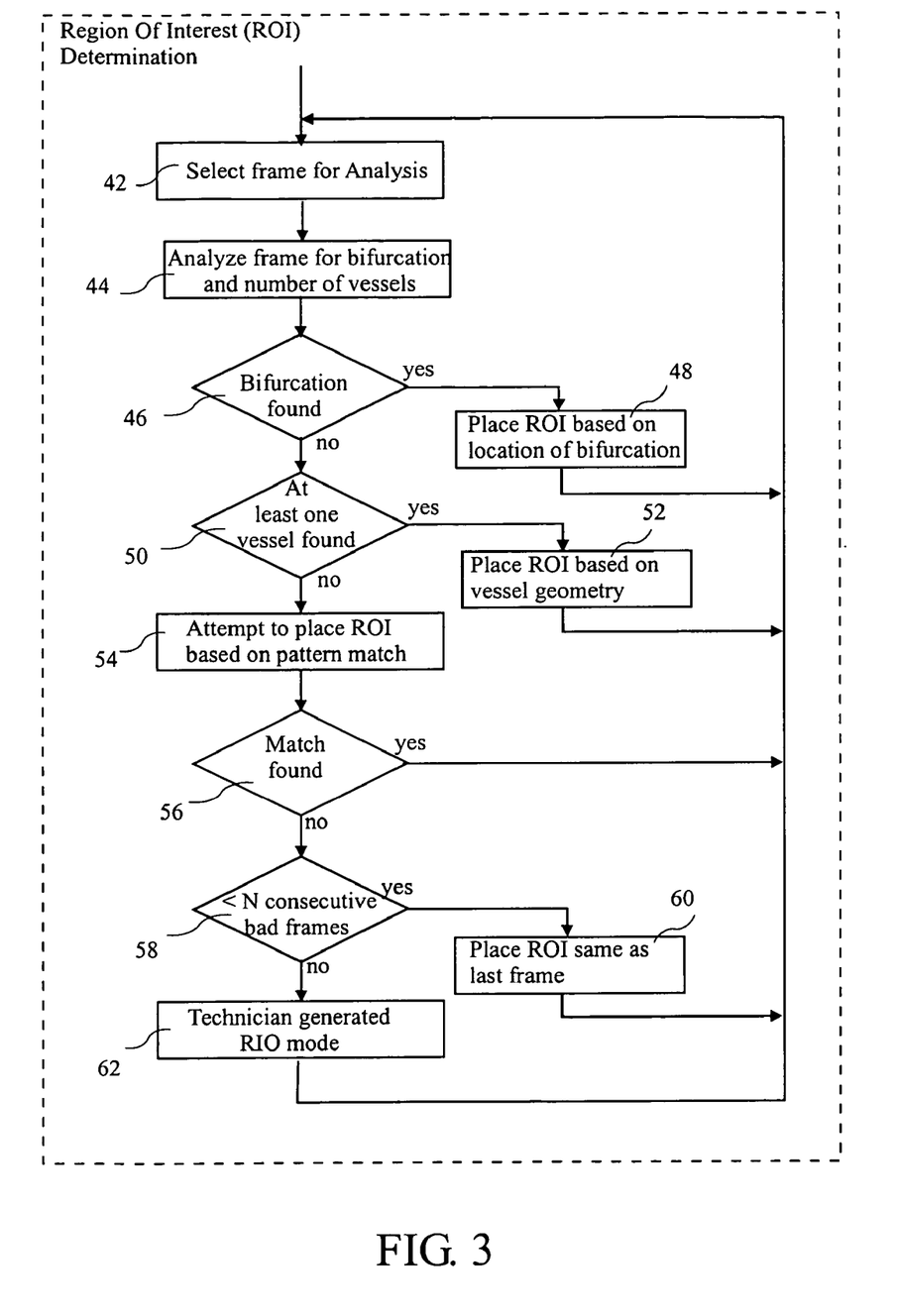
FIG. 3 depicts a flow chart of automated Region Of Interest (ROI) determination.

A method for automated Region Of Interest (ROI) determination according to the present invention is shown in FIG. 3. Ultrasound image data of the carotid artery 30 is collected, for example as depicted in FIG. 2 above, in a format of image frames. The image frames may be provided as digital images, or the image frames may be provided as analog images and processed to generate digital images, and preferably, the image frames may be provided as SVHS images and processed to generate digital images. The image frames are provided to select frame for analysis at 42 where a frame is selected for subsequent processing. The frame is analyzed for bifurcation and number of vessels at 44. If a bifurcation is found at 46, the ROI is placed based on the location of the bifurcation at 48. If a bifurcation is not found, but at least one vessel is found 50, the ROI is placed based on the vessel geometry at 52. If neither bifurcation nor at least one vessel is found, an attempt is made to place the ROI based on a pattern match at 54. If a match was found at 56, a new frame is selected for processing. If a match was not found, and if only a small number of frames have failed to support ROI placement, the ROI is placed as in the previous frame at 58. If more than a small number of frames have failed to support ROI placement, the ROI is generated manually by a technician at 62.

Figure 4A:
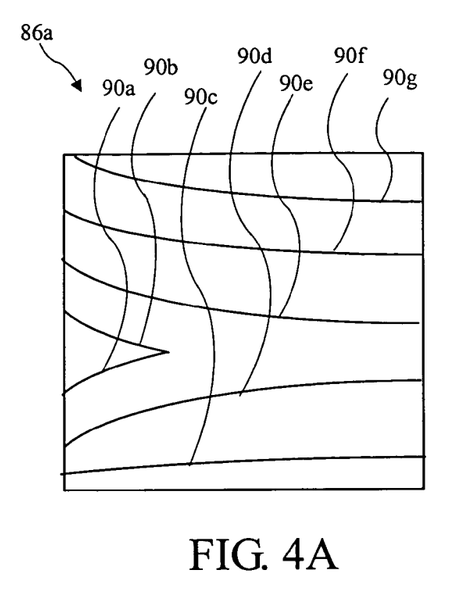
FIG. 4A shows an ultrasound image frame.
Figure 4B:
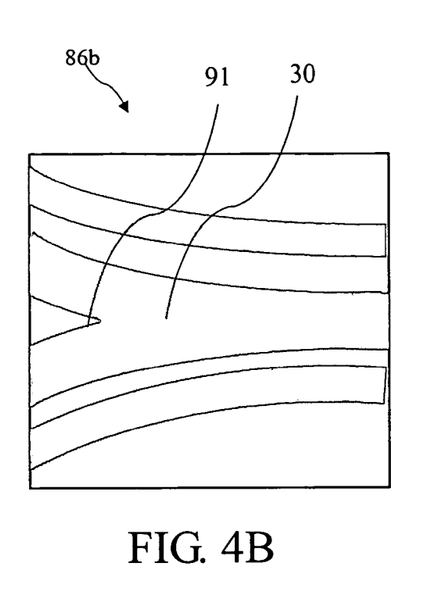
FIG. 4B shows an alternative representation of an ultrasound image.

The image frames are generally provided as rectangular first frame 86a as shown in FIG. 4A. Each frame 86a may include a multiplicity of exemplar bands 90a–90g, and a bifurcation 91 of the carotid artery (FIG. 2). The bands 90a–90g are for purposes of illustration only. The bands in an actual frame may be dark or light, and may be narrow or wide. An example of a second frame 86b displayed to show vessels as broad gray bands is shown in FIG. 4B. The frames 86a and 86b preferably comprise a rectangular array of pixels.

Figure 4C:
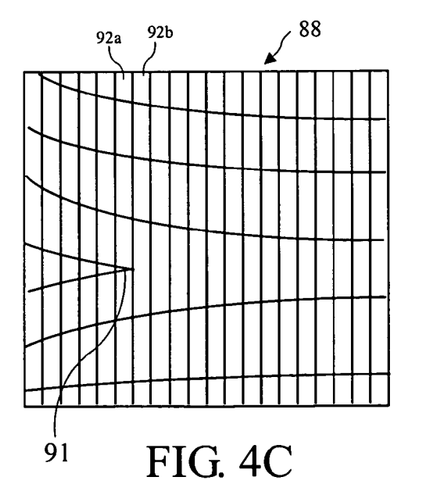
FIG. 4C shows how the image of FIG. 4A may be sliced into slices for processing according to the method of the present invention.

The frames 86a, 86b may be vertically sliced into a multiplicity of slices 88 as shown in FIG. 4C, which slices are preferably two pixels wide. A first slice 92a and a second slice 92b are labeled, which slices 92a, 92b straddle the bifurcation 91. The slices 92a, 92b are processed to identify the presence of stripes. A stripe comprises three bands, a dark band with light bands both above and below the dark band, which light bands correspond to vessel walls, and which dark band corresponds to a vessel lumen. Each slice is processed by image processing software which identifies the stripes and computes confidence scores, stripes used in subsequent processing preferably exceed a fifty percent confidence threshold. Commonly available edge detection software may be used for processing the images, preferably the Active-Mil 7.0 toolkit developed by Matrox Electronic System Ltd. in Dorval, Quebec, Canada, or Halcon 6.1 developed by MVTec Software GmbH in Muchen, Germany.

Figure 5:
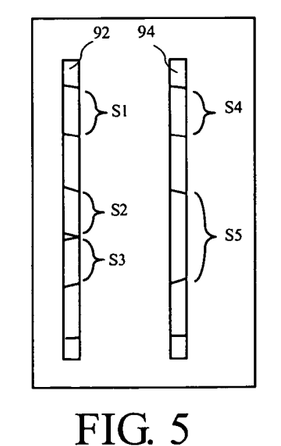
FIG. 5 shows an example of slices which may be compared to determine a position of a bifurcation of the carotid artery.

The slices may be compared to detect the bifurcation of the carotid artery, preferably adjacent slices are compared. If for any reason, adjacent slices can not be singly compared, substantially adjacent slices (i.e., less than 3 slices away) may be compared, or a combination of substantially adjacent slices may be compared (i.e., an averaging of features). For example, the first slice 92a and second slice 92b maybe compared as shown in FIG. 5, wherein Stripes S1, S2, and S3 are identified in slice 92a, and stripes S4 and S5 are identified in slice 92b. If the number of stripes in slice 92a is one more than the number of stripes in slice 92b, and if the top edge stripe S2 corresponds to the top edge of stripe S5, and the bottom edge of stripe S3 corresponds to the bottom edge of stripe S5, a bifurcation 91 is identified. Preferably, the vertical positions of the corresponding edges will be within five percent of each other.

Figure 6:
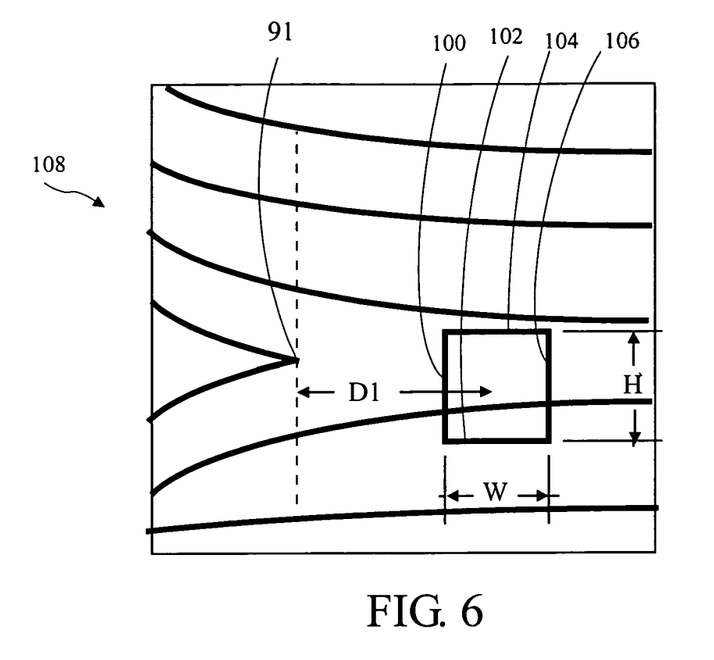
FIG. 6 depicts the placement of the ROI relative to the bifurcation of the carotid artery.

If the bifurcation 91 is identified, the ROI is horizontally centered approximately 2.0 centimeters before the bifurcation, shown by dimension D1 in FIG. 6. The ROI defines a top edge 104, a bottom edge 102, a right edge 106, and a left edge 100. The ROI is preferably approximately 0.5 centimeters wide (W), and preferably approximately 0.5 centimeters high (H), and is vertically positioned with a top edge 104 approximately 0.3 centimeters above highest point of a bottom vessel wall (i.e., the far wall) within the horizontal range of the ROI, of the vessel containing the bifurcation.

Figures 7, 8:
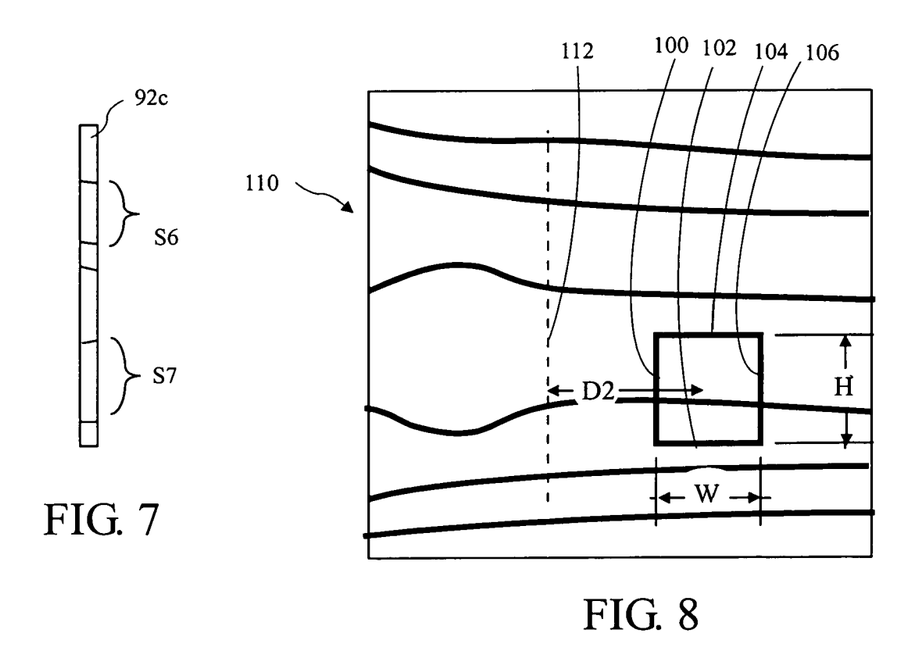
FIG. 7 depicts a single slice suitable for processing to determine a number of stripes (or vessels) in the slice.
FIG. 8 depicts the placement of the ROI relative to a bulb of the carotid artery

In some cases, the bifurcation may not be successfully identified. In these cases, the slices may be processed to attempt to identify the bulb of the carotid artery. The number of stripes (or vessels) in each slice, for example in a third slice 92c as shown in FIG. 7, is computed. An average number of stripes in the frame is computed by averaging the number of stripes in all of the slices within the frame, preferably the average number of stripes in computed using stripes with high confidence, and more preferably the average number of stripes is computed using stripes having at least a fifty percent confidence score.

A rounded average number of stripes is computed by rounding the average to the nearest whole number. The mean and variance of the number of stripes is computed relative to the rounded average number of stripes. The rounded average number of stripes is tagged as valid if the mean is below a mean_threshold, and the variance is below a var_threshold. The mean_threshold is preferably approximately 0.25, and the var_threshold is preferably approximately 1.0.

The minimum confidence level of the stripes within each slice is compared to a min_con_threshold. Slices having one or more stripes with a confidence level below the min_con_threshold are tagged as outliers, and not used in subsequent computations. A second variance is computed based on the remaining slices, and the second variance is compared to a second_var_threshold. An average confidence level is computed for the remaining stripes and compared to an avg_con_threshold. If either the second variance is greater than the second_var_threshold, or the average confidence is less than the avg_con_threshold, the average number of stripes is tagged as invalid. The second_var_threshold is preferably approximately 1.0, and the avg_con_threshold is preferably approximately 75 percent.

If a valid number of stripes is computed, average stripes is set to the rounded average number of stripes, and an attempt is made to use the resulting value to determine the position of the bulb 34 of the carotid artery 30 (see FIG. 2). The portion of the carotid artery below the bulb is referred to as the Common Carotid Artery (CCA). If the average_stripes is three or more, the stripe that is next to the bottom is tagged as a selected stripe. If the average_stripes is two, the bottom stripe is tagged as the selected stripe. If the average_stripes is one, the one stripe in each slice with a single stripe is tagged as the selected stripe.

In each of the three cases described above, one or more of the slices may have a number of stripes different from the average_stripes. In this case, initially, the stripes are selected from the slices having a number of stripes equal to the average_stripes. Stripe position is set to the average of the positions of the tagged stripes. The stripe in the remaining slices (i.e., slices with more than one stripe) which overlaps the stripe position is tagged as the selected stripe. If no stripe overlaps the stripe position, the slice is not used for subsequent processing.

A moving average of the stripe diameters is computed using several consecutive selected stripes, the number of consecutive selected stripes is preferably between five and fifteen, and the number of consecutive selected stripes is more preferably ten. Consecutive averages are compared. If the average increases by at least ten percent, the bulb position 112 is set to the position of the center slice from the average, as shown in FIG. 8. A second ROI 110a is horizontally centered approximately 1.25 centimeters below the bulb (shown as D2). The ROI 110a is vertically centered 0.05 centimeters above the highest point of the far wall of the carotid artery (i.e., the bottom of the selected stripe of the frame) within the horizontal range of the ROI 110a. The ROI 110a width (W) is preferably approximately 0.5 centimeters and the ROI 110a height (H) is preferably approximately 0.5 centimeters.

Figure 9:
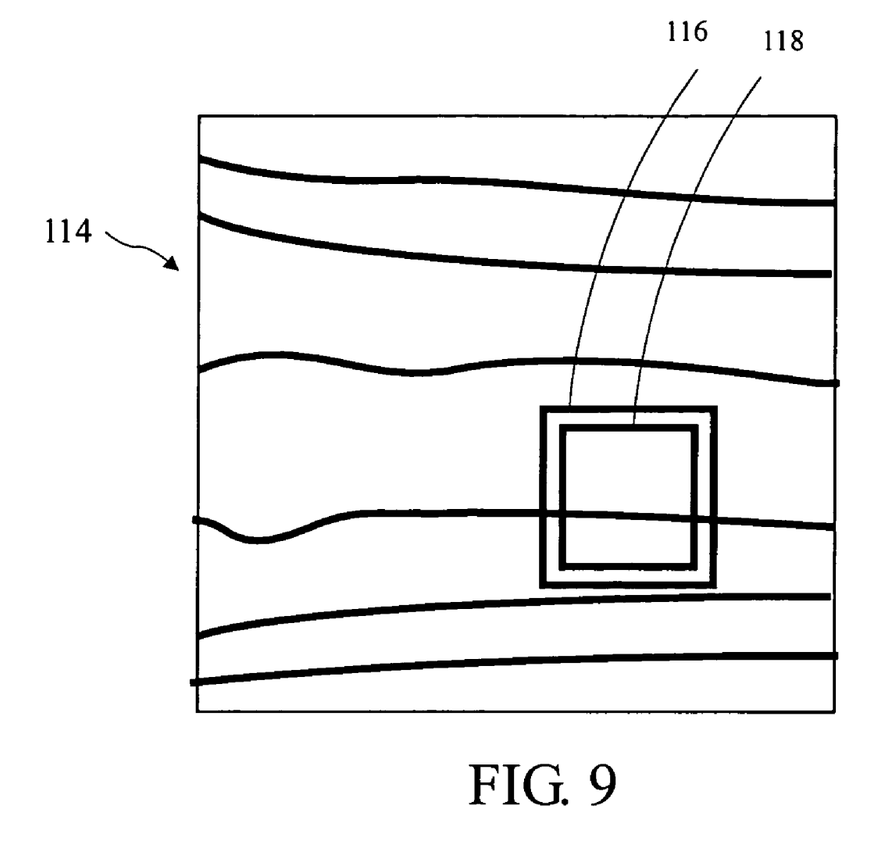
FIG. 9 depicts placement of an expanded region for a pattern match around a previously determined ROI.

If neither the bifurcation nor the bulb are found, a pattern match may be attempted within a failed frame 114 to position the ROI as shown in FIG. 9. An expanded ROI horizontal extent is set to the previous horizontal extent expanded horizontally by a factor of approximately 1.2. An expanded ROI vertical extent is set to the previous vertical extent expanded vertically by a factor of approximately 1.2. The ROI center is set to the center of the previous ROI. A pattern match is then performed in the expanded region 116 to find an area that matches the previous ROI 118. Preferably, pattern-matching is performed using the Matrox Toolkit, or the MVTec toolkit.

If neither the bifurcation, nor the bulb, nor a pattern match are found, and if only a small number of consecutive failures have occurred, the ROI is set to the previous ROI, otherwise, the ROI is manually determined by a technician.

Figure 10:
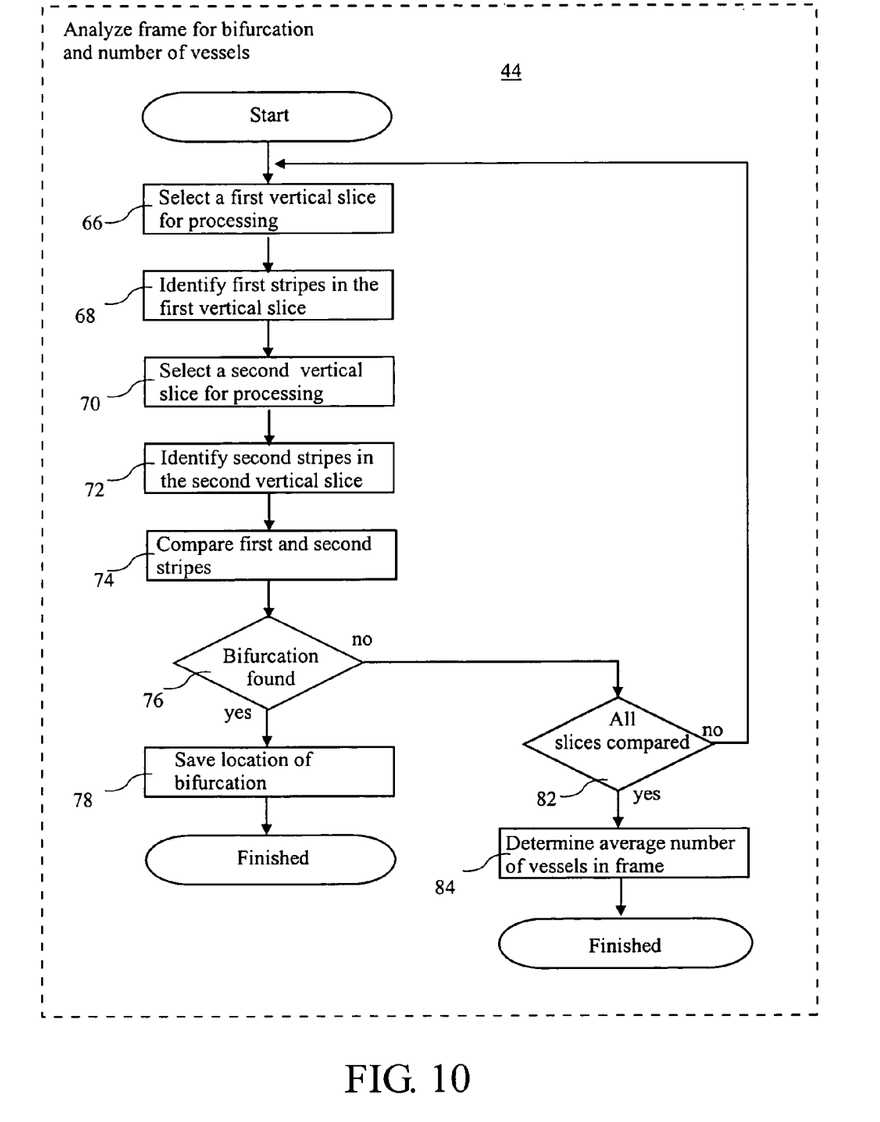
FIG. 10 shows a flow chart of a method for analyzing a frame to find the bifurcation and/or the number of vessels within the frame.

A method for analyzing a frame for bifurcation 44 is shown in FIG. 10. A first vertical slice is selected for processing at 66, and first stripes in the first slice are identified at 68. A second vertical slice is selected for processing at 70, and second stripes within the second slice are identified at 72. The first and second stripes are compared to attempt to determine if the bifurcation occurs substantially between the first and the second slice at 74 (i.e., the bifurcation is in the region substantially overlapping the first and second slices). If the bifurcation is found at 76, the bifurcation location is saved at 78. Otherwise, if all slices have been compared at 82, the average number of slices (i.e., vessels) is computed and saved at 84. Otherwise, the processing starting with select a first vertical slice 66 is repeated for new first and/or second slices.

Figure 11:
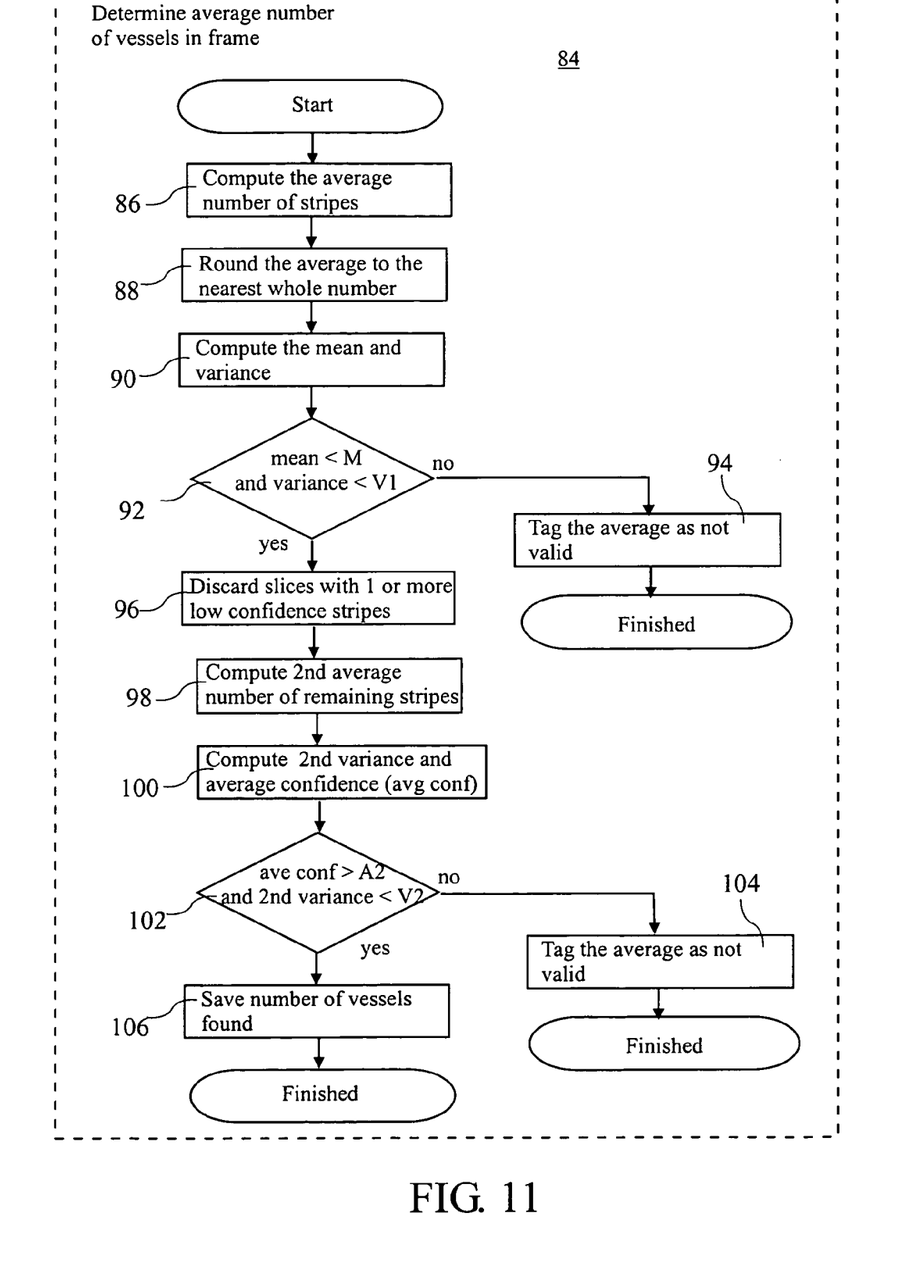
FIG. 11 shows a flow chart of a method for analyzing a frame to find an average number of vessels in the frame.

A method for determining an average number of vessels in a frame 84 (see FIG. 10) is shown in FIG. 11. An average number of stripes is computed at 86. A rounded average number of stripes is computed from the average number of stripes at 88. The mean and variance of the number of stripes is computed at 90. If the mean is not below a mean threshold M (preferably 0.25) and the variance is not below a first variance threshold V1 (preferably 1.0) at 92, the average is tagged as not valid at 94. Otherwise, slices with one or more low confidence stripes are discarded at 96. A second average number of stripes is computed from remaining slices at 98. A second variance and average confidence are computed at 100. If the average confidence is below a threshold (preferably seventy five percent) and the second variance is above a second variance threshold (preferably 1.0) at 102, the average is tagged as not valid at 104. Otherwise, the number of vessels is saved for subsequent processing at 106.

Figure 12:
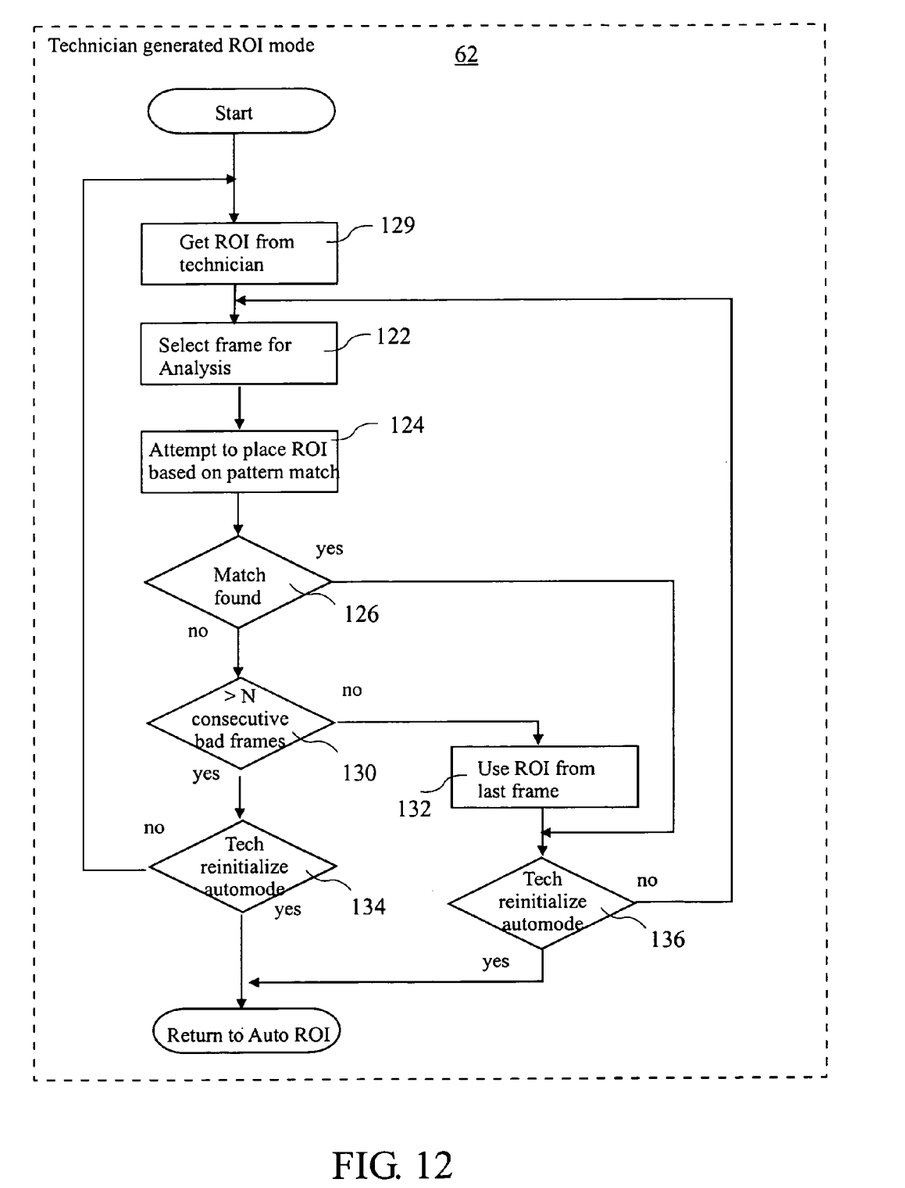
FIG. 12 shows a flow chart of a method for technician-generated ROI.

A method for technician-generated ROI 62 (see FIG. 3) is shown in FIG. 12. The ROI is determined by the technician at 129. A new frame is selected for analysis at 122. A pattern match is attempted at 124, which match is similar to the match described in FIG. 9 above. If a match is found at 126, the technician may reinitialize automatic ROI determination. If automatic ROI determination is reinitialized at 136, automode is returned to, otherwise another new frame is selected at 122 and the processing described above is repeated.

If a match was not found at 126, and more than a small number of frames have failed to result in a matching pattern at 130, and the technician does not reinitialize automode at 134, the ROI is determined by the technician at 129, and the processing above is repeated. If a match was not found at 126, and more than a small number of frames have failed to result in a matching pattern at 130, and the technician does reinitialize automode at 134, the automode is returned to. If a match was not found at 126, and more than a small number of frames have not failed to result in a matching pattern at 130, the ROI is determined to be the ROI from the previous fame at 132, the technician may reinitialize automode at 136 and return to automode, or the technician may not reinitialize automode at 136, and a frame is selected for analysis at 122. And the processing described above is repeated.

INDUSTRIAL APPLICABILITY

The present invention finds industrial applicability in the field of automated determination of a Region Of Interest (ROI) within an Image. More particularly, the present invention finds industrial applicability in the field of automated determination of an ROI of an ultra sound image of a carotid artery.

SCOPE OF THE INVENTION

While the invention herein disclosed has been described by means of specific embodiments and applications thereof, numerous modifications and variations could be made thereto by those skilled in the art without departing from the scope of the invention set forth in the claims.

What is claimed is:

1. A method for defining a Region Of Interest (ROI) of a carotid artery for measuring the arterial wall thickness in a patient, comprising:
   providing at least one image including a portion of the carotid artery;
   slicing the image into vertical slices;
   selecting a stripe which corresponds to the Common Carotid Artery (CCA), within each of the slices;
   computing a size of each selected stripe;
   comparing the sizes of the selected stripes;
   identifying a base of a bulb of the carotid artery as corresponding to the stripe having at least a minimum increase in size compared to stripes in lower slices;
   positioning the ROI below the base of the bulb, and measuring the arterial wall thickness of the patient in the ROI.

2. The method of claim 1 wherein selecting a stripe which corresponds to the CCA, within each of the slices, comprises selecting a stripe which corresponds to the CCA based on the order of the stripe within the slice.

3. The method of claim 1, wherein selecting the stripe which corresponds to the CCA, within each of the slices, comprises:
   comparing the number of stripes within each of the slices to determine which slices have a valid number of stripes; and
   selecting the stripe which corresponds to the CCA, within each of the slices having a valid number of stripes.

4. The method of claim 1 wherein positioning an ROI with respect to the base of the bulb comprises positioning the ROI horizontally centered approximately 1.25 centimeters below the base of the bulb.

5. The method of claim 4, further including vertically centering the ROI approximately 0.05 centimeters above the highest point of a far wall of the carotid artery within a horizontal extent of the ROI.

6. The method of claim 5, wherein positioning an ROI comprises positioning an ROI having an approximately 0.5 inch height and an approximately 0.5 inch width.

7. The method of claim 1 wherein computing a size of each selected stripe comprises computing a diameter of each selected stripe.

8. The method of claim 1 wherein comparing the sizes of the selected stripes comprises comparing averages of the sizes of the selected stripes of consecutive slices to averages of the sizes of the selected stripes of lower consecutive slices.

9. The method of claim 8 wherein selecting the slice including the stripe corresponding to at least a minimum increase in size compared to lower slices comprises selecting the slice including the stripe corresponding to at least an approximately ten percent increase in average size compared to lower slices.

10. The method of claim 1 further including, if the base of the bulb is not identified, providing a technician-generated ROI.

11. A method for determining a Region Of Interest (ROI) for subsequent Intima Media Thickness (IMT) analysis in a patient, the method comprising:
   providing at least one digital frame of a portion of a carotid artery, wherein the frame includes at least one of a set consisting of a bulb of the carotid artery and a bifurcation of the carotid artery;
   automatically processing the frame to identify the ROI in the frame, the automatically processing comprising at least one of the set consisting of:

determining the ROI by detecting a bifurcation of the carotid artery, the determining comprising:
  slicing the frame into vertical slices;
  automatically comparing at least one of the vertical slices to at least one other of the vertical slices to find the bifurcation of the carotid artery;
  determining the ROI horizontal extent to range from approximately 1.75 cm below the bifurcation to approximately 2.25 cm below the bifurcation;
  identifying the highest point of a far wall segment of the carotid artery within the ROI horizontal extent; and
  determining the ROI vertical extent to range from approximately 0.3 cm above the highest point to approximately 0.2 cm below the highest point; and
determining the ROI by detecting a bulb of the carotid artery, the determining comprising:
  slicing the frame into vertical slices;
  automatically comparing at least one of the vertical slices to at least one other of the vertical slices to find the bulb of the carotid artery;
  determining the ROI horizontal extent to range from approximately 1.0 cm below the bulb to approximately 1.5 cm below the bulb;
  identifying the highest point of a far wall segment of the carotid artery within the ROI horizontal extent; and
  determining the ROI vertical extent to range from approximately 0.3 cm above the highest point to approximately 0.2 cm below the highest point; and
determining the ROI by pattern-matching a portion of the frame to a previous ROI having a previous horizontal extent and a previous vertical extent; the determining comprising:
  determining an expanded ROI horizontal extent to be the previous horizontal extent expanded horizontally by a factor of approximately 1.2;
  determining an expanded ROI vertical extent to be the previous vertical extent expanded vertically by a factor of approximately 1.2;
  performing an automatic pattern match comparing the previous ROI to the region defined by the expanded ROI horizontal extent and the expanded ROI vertical extent; and
  determining the ROI based on the highest correlation of the automatic pattern match, and thereafter analyzing the Intima Media Thickness(IMT) in said ROI in said patient.

12. A system for processing ultrasound images of the carotid artery, comprising:
  an ultrasound sensor;
  an ultrasound apparatus adapted to generate frames;
  a sensor cable connecting the ultrasound sensor to the ultrasound apparatus,
wherein the ultrasound apparatus is adapted to receive measurements from the ultrasound sensor, and wherein the ultrasound apparatus is further adapted to process the measurements to generate ultrasound data;
  a computer; and
  a path adapted to carry the ultrasound data from the ultrasound apparatus to the computer, wherein the path is selected from a group consisting of dedicated cables, phone lines, a Local Area Network (LAN), the Internet, and a wireless path,
wherein the computer is adapted to pre-process the ultrasound data to generate Regions Of Interest (ROIs) within the data for subsequent processing, wherein the ROIs are subsets of the ultrasound data.

13. A method for defining a Region Of Interest (ROI) of the carotid artery for measuring the arterial wall thickness in a patient, comprising:
  providing at least one image of a portion of the carotid artery;
  slicing the image into vertical slices;
  identifying stripes within each slice, which stripes correspond to vessels; and
  identifying a bifurcation of the carotid artery when two stripes in a higher first slice correspond to one stripe in a lower second slice,
  positioning the ROI below the bifurcation, and
  measuring the arterial wall thickness of the patient within the ROI.

14. The method of claim 13, wherein identifying a bifurcation of the carotid artery when two stripes in the first slice correspond to one stripe in the second slice comprises identifying a bifurcation of the carotid artery when two stripes in the first slice correspond to one stripe in the second slice, wherein each of the two stripes in the first slice a least partly overlap the one stripe in the second slice.

15. The method of claim 13, wherein identifying stripes within each slice comprises identifying three bands comprising:
  a dark band corresponding to a vessel lumen; and
  light bands above and below the dark band, wherein the light bands correspond to vessel walls.

16. The method of claim 13, wherein identifying a bifurcation of the carotid artery when two stripes in the first slice correspond to one stripe in the second slice comprises identifying a bifurcation of the carotid artery when two stripes in the first slice correspond to one stripe in a substantially adjacent second slice.

17. The method of claim 13 wherein identifying a bifurcation of the carotid artery when two stripes in the first slice correspond to one stripe in the second slice includes:
  identifying if the first slice includes more stripes than the second slice, which first slice is above of the second slice;
  identifying if a first top edge of a higher stripe in the first slice corresponds to a second top edge of a single stripe in the second slice; and
  identifying if a first bottom edge of a lower stripe in the first slice corresponds to a second bottom edge of the single stripe in the second slice.

18. The method of claim 13 wherein positioning the ROI with respect to the bifurcation comprises positioning the ROI horizontally centered approximately two centimeters below the bifurcation.

19. The method of claim 18 wherein positioning the ROI with respect to the bifurcation comprises positioning the ROI to range horizontally between approximately 1.75 cm below the bifurcation and approximately 2.25 cm below the bifurcation.

20. The method of claim 19 wherein positioning the ROI with respect to the bifurcation further comprises:
  identifying a highest point of a far wall segment of the carotid artery within the ROI horizontal range; and
  positioning the ROI vertically centered approximately 0.05 cm above the highest point.

21. The method of claim 20 wherein positioning the ROI with respect to the bifurcation further comprises positioning the ROI to range vertically from approximately 0.3 cm above the highest point to approximately 0.2 cm below the highest point.

* * * * *